(12) United States Patent
Nishii et al.

(10) Patent No.: US 8,292,564 B2
(45) Date of Patent: Oct. 23, 2012

(54) PHARMACEUTICAL CONTAINER TRANSFERRING SYSTEM

(75) Inventors: Hisao Nishii, Osaka (JP); Kazuhiro Tsutsumi, Osaka (JP); Jun Ohshimo, Osaka (JP); Hiroyuki Taike, Osaka (JP)

(73) Assignee: Tsubakimoto Chain Co., Osaka (JP)

( * ) Notice: Subject to any disclaimer, the term of this patent is extended or adjusted under 35 U.S.C. 154(b) by 326 days.

(21) Appl. No.: 12/719,966

(22) Filed: Mar. 9, 2010

(65) Prior Publication Data

US 2011/0158777 A1 Jun. 30, 2011

(30) Foreign Application Priority Data

Dec. 25, 2009 (JP) ................................. 2009-295950

(51) Int. Cl.
*B65G 1/00* (2006.01)
(52) U.S. Cl. ..................................... 414/331.02; 422/63
(58) Field of Classification Search .................. 414/277, 414/331.02, 749.5; 422/63, 65, 562
See application file for complete search history.

(56) References Cited

U.S. PATENT DOCUMENTS

| | | | | |
|---|---|---|---|---|
| 6,068,437 A | * | 5/2000 | Boje et al. | 414/331.02 |
| 6,283,693 B1 | * | 9/2001 | Acello et al. | 414/403 |
| 6,472,218 B1 | * | 10/2002 | Stylli et al. | 436/48 |
| 7,829,028 B2 | * | 11/2010 | Elsener et al. | 422/536 |
| 7,892,504 B2 | * | 2/2011 | Taike et al. | 422/562 |
| 2002/0009391 A1 | | 1/2002 | Marquiss | |

FOREIGN PATENT DOCUMENTS

| | | |
|---|---|---|
| EP | 1 361 440 | 11/2003 |
| JP | 11-160325 | 6/1999 |
| JP | 2006-214919 | 8/2006 |
| JP | 2009-042011 | 2/2009 |
| WO | WO2009/085681 | 7/2009 |

* cited by examiner

*Primary Examiner* — Joshua Rudawitz
(74) *Attorney, Agent, or Firm* — Dann, Dorfman, Herrell & Skillman; Henry H. Skillman

(57) ABSTRACT

The present invention provides a pharmaceutical container transferring system suitable for taking containers stored in a storage rack in closely-spaced relation into and out of the storage rack. The system has a storage rack mounting plate for holding the storage rack, a thrust-up member provided underneath of the plate to thrust up a target container through an insertion hole of the storage rack while abutting the bottom of the container, a picking member provided above the mounting plate and having compressible jaw members having a spacing smaller than the upper part of the thrust-up container which are compressed to pinch the incoming container by extending their spacing, an upper thrust-down member disposed vertically above the lower thrust-up member for thrusting down the container pinched by the picking member and a picking carriage provided with the lower thrust-up member, the upper picking member and the upper thrust-down member that sandwich the mounting plate as the carriage moves.

10 Claims, 16 Drawing Sheets

PHARMACEUTICAL CONTAINER TRANSFERRING SYSTEM

FIELD OF INVENTION

The present invention relates to a system for transferring containers for pharmaceutical development (referred to as a 'pharmaceutical container transferring system hereinafter) suitable for taking containers stored in a storage rack in high integration, i.e., in closely-spaced relation, in and out of the storage rack in the field of pharmaceutical research and development and more specifically to a pharmaceutical container transferring system suitable for a 384-tube rack in which a gap between neighboring containers stored in the storage rack is extremely narrow.

BACKGROUND OF THE INVENTION

Heretofore, in the field of pharmaceutical development and research and others, a solution in which a sample is dissolved is injected into a cylindrical container called a micro-tube and a plurality of such micro-tubes are stored vertically in a storage rack, e.g., a storage rack partitioned into 96 sections (8 rows by 12 columns) (referred to as a '96-tube rack hereinafter) as shown in FIG. 15A to store and convey the samples.

Recently, there is also known a storage rack having 384 sections in total (16 rows by 24 columns) as shown in FIG. 15B (referred to as a '384-tube rack' hereinafter) for storing smaller micro-tubes, i.e., super micro-tubes, to store many more samples in the rack having the same outer shape and dimensions as the 96-tube rack conforming to the SBS (Society for Biomolecular Screening) Standard (see description of European Patent Application Laid Open No. 1361440 (FIG. 6) and Japanese Patent Publication No. 3421252 (Paragraph 5 in Page 2)).

Still more, there is known a stationary picking system 700 for picking up a predetermined micro-tube by conveying the 96-tube rack as shown in FIG. 16 (see U.S. Pat. No. 6,838, 051).

Problems to be Solved by the Invention

By the way, the 384-tube rack having four times of storage capacity per rack as compared to the conventional 96-tube rack has a problem that it is difficult to realize a method of gripping a container by inserting a jaw member into a gap between the containers because beside that dimension of a bottom of the container, i.e., super micro-tube, is as small as ½ (¼ in terms of an area) and their integration rate is high, a gap that exists between the neighboring containers of the 96-tube rack for inserting the jaw member to grip the container is extremely narrow in the 384-tube rack.

Still more, when the 384-tube rack is stored in a cold environment, it is difficult to accurately pick up the container one by one because the neighboring containers are frozen to each other.

Then, EPO Patent Document adopts a so-called thrust-down method of thrusting down a target container (384-tube) stored in the 384-tube rack while abutting against an upper surface of a head of the container so that the container penetrates through a storage space of the 384-tube rack and is transferred to another 384-tube rack waiting for the container at right below the container.

There is also proposed a so-called thrust-up method of pushing up the container by means of a thrust-up rod from a floor surface side of the storage rack.

However, the thrust-down method described above has a problem that because the container is pushed in so as to penetrate through the storage space of the storage rack, a large hole is created in the storage space of the storage rack if the container penetrates through the storage space once and another container cannot be stored in that storage space (storing position). Although it may be possible to repetitively store the containers by slightly narrowing each storage space of the storage rack as compared to the dimension of the container and by constructing the storage space by flexible pinching surfaces, there is another problem that a customized storage rack that is expensive as compared to a general storage rack is required.

Still more, although it is possible to pull the container in and out of the storage space just by positioning by the thrust-up method described above in the case of the 96-tube rack, there are problems that how to grasp the storage rack so that the storage rack is not pushed up together with the container and how to accurately position the storage rack in the case of the 384-tube rack.

When a container anchoring recess provided on the sidewall of the bottom of the container so that the container will not fall down even if the storage rack is turned around is engaged with a container anchoring projection provided on the inner side surface of the insertion hole at the bottom of the storage rack, a considerably large upward force is applied to the storage rack when the container is pushed up by the thrust-up rod from the floor surface side of the rack. Accordingly, it is an important problem how to hold the storage rack against displacement.

Still more, there is a problem that all claw members for grasping the storage rack must be arranged so that they do not interfere the storage rack and so that the storage rack may be move up as it is when the storage rack is released.

Further, it is demanded to cut the space and cost of the system by reducing a number of actuators necessary for moving and driving the claw members for grasping and releasing the storage rack as much as possible.

The picking system disclosed in U.S. Pat. No. 6,828,051 has a problem that, because a storage tray is moved to pick up the container, the system is complicated and may disturb the contents of the container because the storage tray must be moved accurately from side to side to transfer the container among the plurality of storage trays.

Accordingly, the present invention aims at solving the technological problems described above by providing a pharmaceutical container transferring system suitable for accurately taking in and out containers stored closely spaced in a storage rack such as the 384-tube rack.

The invention also aims at providing a pharmaceutical container transferring system that is arranged so as to steadily grasp the storage rack when the container is pulled out, so that all claw members for grasping the storage rack do not interfere with the storage rack when the storage rack is released and so that the system size and cost may be cut.

Means for Solving the Problems

As a result of ardent study which the inventors made to solve the technological problems described above, the inventors obtained a novel finding that the invention brings about remarkable effects that are hardly predictable from the conventional system by having picking and rack holding mechanisms having novel structures and consummated the invention based on such finding.

A first aspect of the invention solves the aforementioned problems by a pharmaceutical container transferring system for vertically storing a plurality of containers by inserting containers of pharmaceutical samples in matrix in a storage rack having insertion holes that fit with the shape of the lower part of the containers to support the container and for taking a selected container out of the storage rack to store the container into a target storage position within the storage rack, having:

a rack holding mechanism for holding the storage rack in a horizontally installed storage rack mounting plate;

a thrust-up member provided underneath of the storage rack mounting plate to thrust up the container through the insertion hole of the storage rack while abutting with the bottom of the target container;

a picking member provided above the storage rack mounting plate and having compressible jaw members having a spacing smaller than the dimension of the upper part of the thrust-up container to pinch the incoming container corresponding to the thrust-up operation of the thrust-up member by extending the spacing of the jaw members;

a thrust-down member disposed in vertical registry with the thrust-up member for thrusting down the container pinched by the picking member; and a picking carriage provided with the thrust-up member, picking member and thrust-down member that moves while sandwiching the storage rack mounting plate.

A second aspect of the invention solves the aforementioned problems further by arranging the pharmaceutical container transferring system of the first aspect such that the length in the longitudinal direction of the jaw member is longer than the whole length of the container.

A third aspect of the invention solves the aforementioned problems by arranging the pharmaceutical container transferring system of the first or second aspect such that a co-lift preventing member is positioned above the storage rack mounting plate to abut with the upper surface of the head of the surrounding containers so that the surrounding containers are not lifted up together with the container thrust-up by the thrust-up member.

A forth aspect of the invention solves the aforementioned problems further by arranging the pharmaceutical container transferring system of any one of the first through third aspects such that the storage rack mounting plate has a plurality of storage rack mounting areas and rack holding mechanisms are disposed at each of the storage rack mounting areas.

A fifth aspect of the invention solves the aforementioned problems further by arranging the pharmaceutical container transferring system of the first through fourth aspects such that the storage rack has a flange around peripheral edge of the bottom thereof; and the rack holding mechanism comprises stationary guides for pressing and supporting one side surface of the storage rack;

movable floating preventing claws provided so as to movably face to each other at two neighboring side surfaces different from one side surface of the storage rack and engaging with the flange of the storage rack when they move forward; and stationary floating preventing claws containing extrusion pins that abut with the flange of the storage rack and retract when the movable floating preventing claws move forward by facing to the remain one side surface of the storage rack and extend when the movable floating preventing claws retract to push back the flange of the storage rack.

A sixth aspect of the invention solves the aforementioned problems further by arranging the pharmaceutical container transferring system of the first through fifth aspects with storage racks and containers which have a container anchoring recess on the sidewall of the bottom thereof;

the storage rack has a container anchoring projection on the inner side surface of the through hole; and the container anchoring recess fits with the container anchoring projection when the container is stored in the storage rack.

Advantages of the Invention

By having the structures as described above, the present invention may bring about the remarkable effects corresponding to the peculiar structure as described below.

According to first aspect of the invention, the pharmaceutical container transferring system for vertically storing a plurality of containers for injecting samples for pharmaceutical development in matrix in the storage rack having the insertion holes that fit with the shape of lower part of the container to support the container and for taking a selected one container out of the storage rack or storing the container into the target storage position within the storage rack includes a rack holding mechanism for holding the storage rack in a horizontally installed storage rack mounting plate, a thrust-up member provided underneath of the storage rack mounting plate to thrust up the selected container through the insertion hole of the storage rack while abutting with the bottom of the selected container, a picking member provided above the storage rack mounting plate and having compressible jaw members having a spacing smaller than the dimension of the upper part of the thrust-up container to pinch the incoming container corresponding to the thrust-up operation of the thrust-up member by extending its width, a thrust-down member disposed vertically on the thrust-up member for thrusting down the container pinched by the picking member and a picking carriage provided with the thrust-up member, picking member and thrust-down member that moves while sandwiching the storage rack mounting plate.

Accordingly, because it is unnecessary to insert the jaw member between the neighboring containers, the container stored in the highly integrated storage rack such as the 348-tube rack that substantially has no gap between the neighboring containers may be accurately taken in and out of the storage rack.

According to second aspect of the invention, the pharmaceutical container transferring system of the first aspect is arranged such that the length in the longitudinal direction of the jaw member is longer than the whole length of the container, so that the picking member can have a plurality of containers and the efficiency in transferring the containers from one storage rack to another storage rack may be remarkably improved.

According to third aspect of the invention, the pharmaceutical container transferring system of the first or second aspect is arranged such that a co-lift preventing member is disposed above the storage rack mounting plate to abut with the upper surface of the head of the surrounding containers so that the surrounding containers are not lifted up together with the container thrust-up by the thrust-up member, so that even if the neighboring containers are frozen to each other, they are prevented from being lifted up together and the pharmaceutical containers stored in very low temperature may be transferred very accurately.

According to fourth aspect of the invention, the pharmaceutical container transferring system of anyone of the first through third aspects is arranged such that the storage rack mounting plate has the plurality of storage rack mounting areas and the rack holding mechanisms are disposed at the respective storage rack mounting areas, so that the container may be transferred not only in one storage rack but also among the plurality of storage racks. Accordingly, the invention can remarkably improve a so-called high through-put screening (HTS) technology of very effectively carrying out operations of finding a new medicinal effect by randomly screening chemical compounds.

According to fifth aspect of the invention, the pharmaceutical container transferring system of the first through fourth aspects is arranged such that the storage rack has a flange around peripheral edge of the bottom thereof and the rack holding mechanism has stationary guides for pressing and supporting one side surface of the storage rack, movable floating preventing claws provided so as to movably face two neighboring side surfaces different from one side surface of the storage rack and engaging with the flange of the storage rack when move forward and stationary floating preventing claws containing extrusion pins that abut with the flange of the storage rack and when the movable floating preventing claws move forward by facing to the remain one side surface of the storage rack and extend when the movable floating preventing claws retract to push back the flange of the storage rack.

Accordingly, because the movable and stationary floating preventing claws provided at the three side surfaces of the storage rack firmly grasp the storage rack so that the storage rack is not lifted up when the container is pulled out, it is possible to prevent the container from being erroneously transferred. Still more, when the storage rack is released, the storage rack is slid in the horizontal direction by the extrusion pin biased by elastic force of the spring so that the storage rack may be moved upward as it is and the storage rack is disengaged from the stationary floating preventing claws without being interfered by the floating preventing claws. Accordingly, it is possible to steadily prevent the storage rack from being erroneously transferred.

Still more, because what needs to be driven to move back and fourth among the claw members for grasping and releasing the storage rack are only the movable floating preventing claws provided at the neighboring two side surfaces among the four side surfaces of the storage rack, only two actuators are necessary. Accordingly, the space and cost of the system may be cut.

According to sixth aspect of the invention, the pharmaceutical container transferring system of the first through fifth aspects includes modified racks and containers, such that the container has the container anchoring recess on the sidewall of the bottom thereof, the storage rack has the container anchoring projection on the inner side surface of the through hole and the container anchoring recess fits with the container anchoring projection when the container is stored in the storage rack, so that even though a considerably large force of pushing up the storage rack acts when the container is pulled out of the storage rack, the container may be steadily transferred because the storage rack is steadily grasped and secured.

BRIEF DESCRIPTION OF DRAWINGS

FIG. 9b is a section view of the storage rack and the container taken along a line IXB-IXB in FIG. 9a;

BEST MODE FOR CARRYING OUT THE INVENTION

One exemplary mode for carrying out the invention will be explained below with reference to FIGS. 1 through 15.

Figure 8:
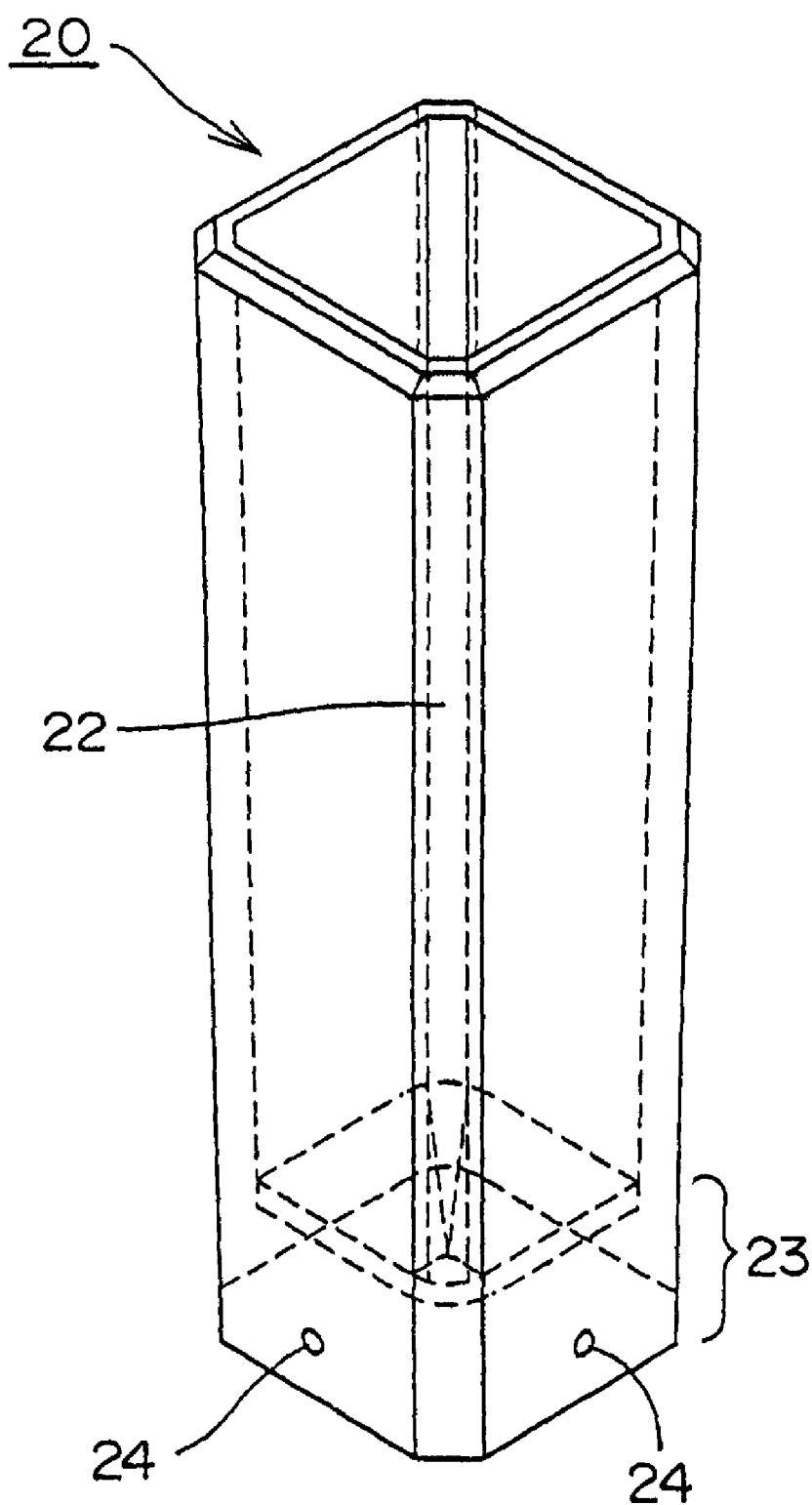
FIG. 8 is a perspective view of the container (micro-tube) that is to be transferred by the pharmaceutical container transferring system of the invention.
Figure 15A:
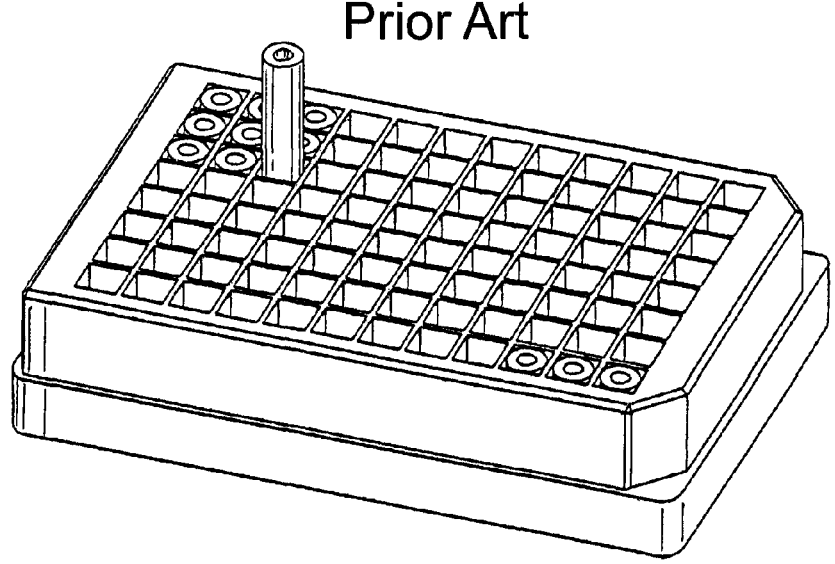
FIG. 15a is a perspective view showing prior art containers and storage rack and FIG. 15b is a perspective view showing containers and storage rack of the invention.
Figure 15B:
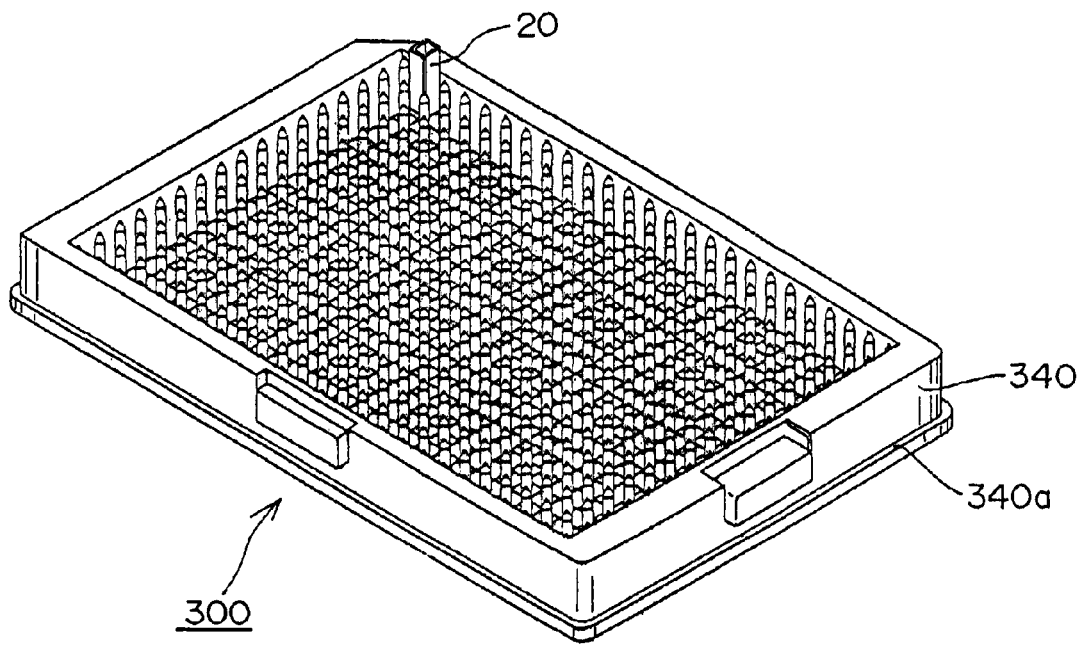
Figure 16:
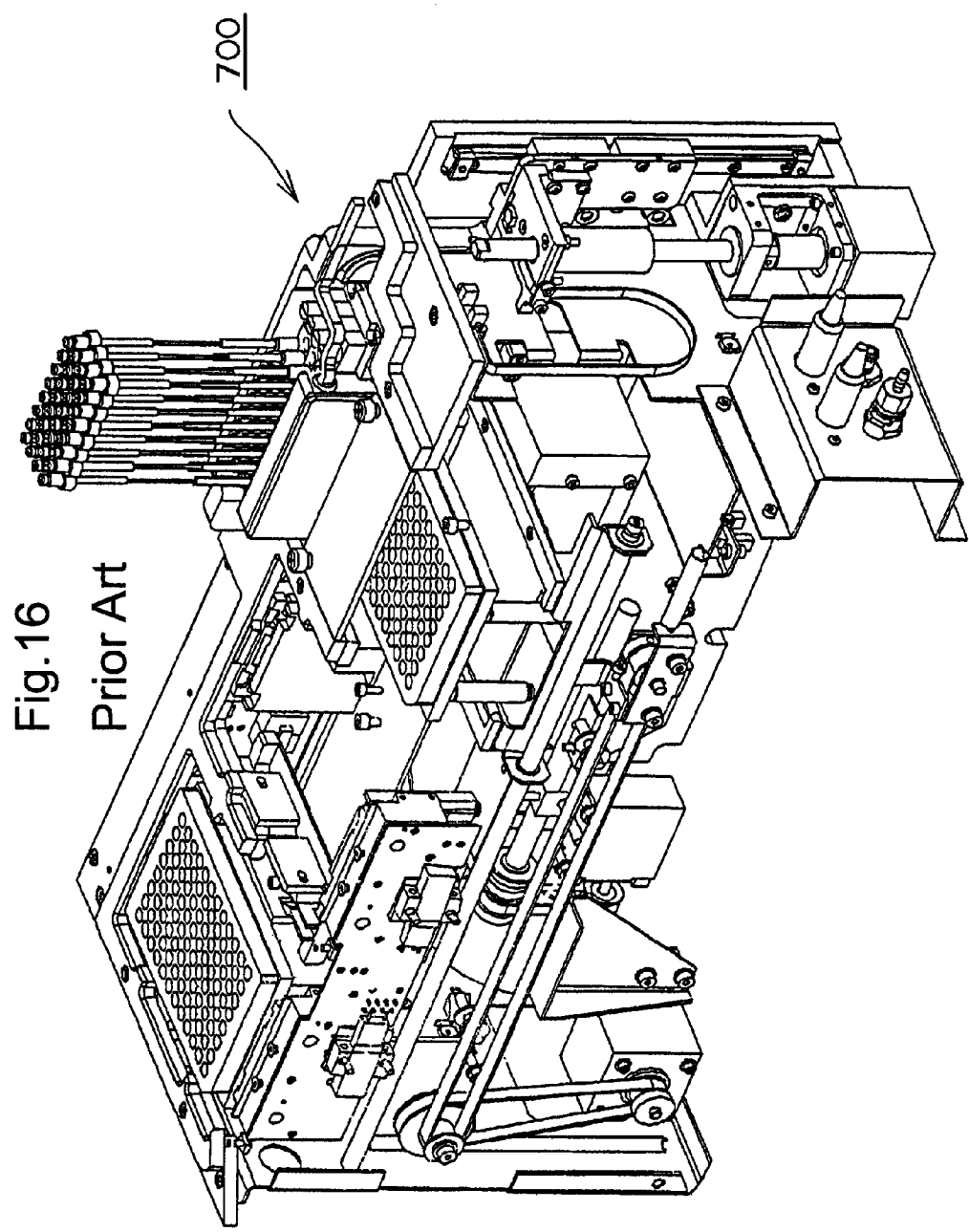
FIG. 16 is a perspective view of a prior art container transferring system.

As shown in FIG. 15b, a storage rack 300 of the invention has a rack frame 340 that composes an outer frame of the storage rack 300 and a low height grid bottom 320 partitioned in grid as shown in FIG. 9 within the frame. The storage rack 300 can vertically store a plurality of containers 20 by fitting each one section of the grid bottom 320 with a sidewall 23 of the bottom of the container (micro-tube) 20 as shown in FIG. 8. The storage rack 300 has a rectangular storage surfaces and has a flange 340a around the peripheral edge of the bottom as shown in FIG. 15b.

Further, as shown in FIG. 9, a vertically uprising container supporting pin 330 is vertically provided from each intersection of the grid of the grid bottom 320. The container supporting pin 330 has a horizontally circular section and is tapered such that the higher the height, the thinner the diameter is.

The container 20 to be transferred by the pharmaceutical container transferring system 100 of the invention has a rectangular tubular shape as shown in FIG. 8. It is thinned toward the bottom and corners where the outer side surfaces meet are chamfered with an angle of 45°, as indicated at 22 in FIG. 8.

Figure 9A:
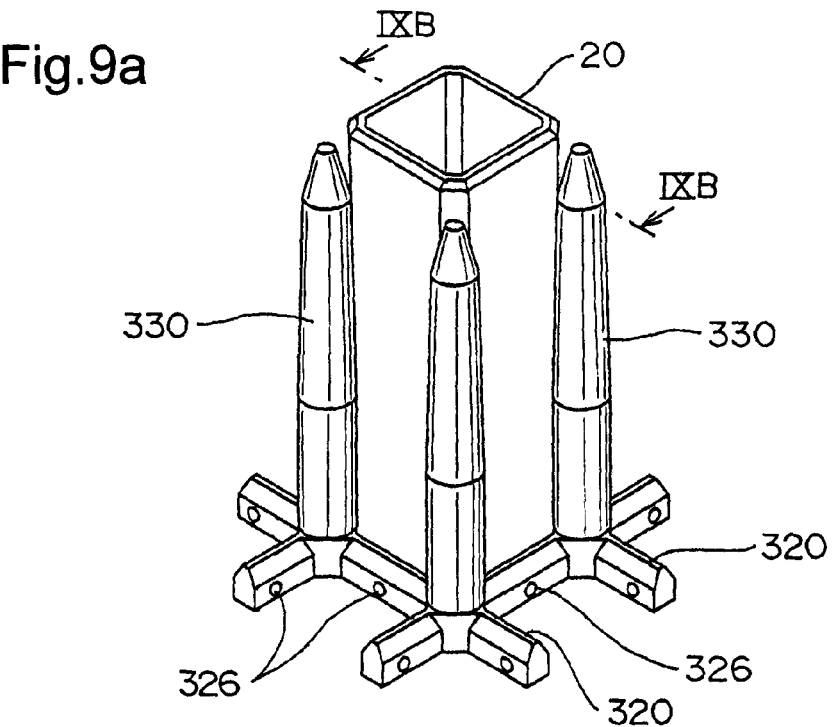
FIG. 9a is a perspective view showing one section of the storage rack for storing the containers shown in FIG. 8
Figure 9B:
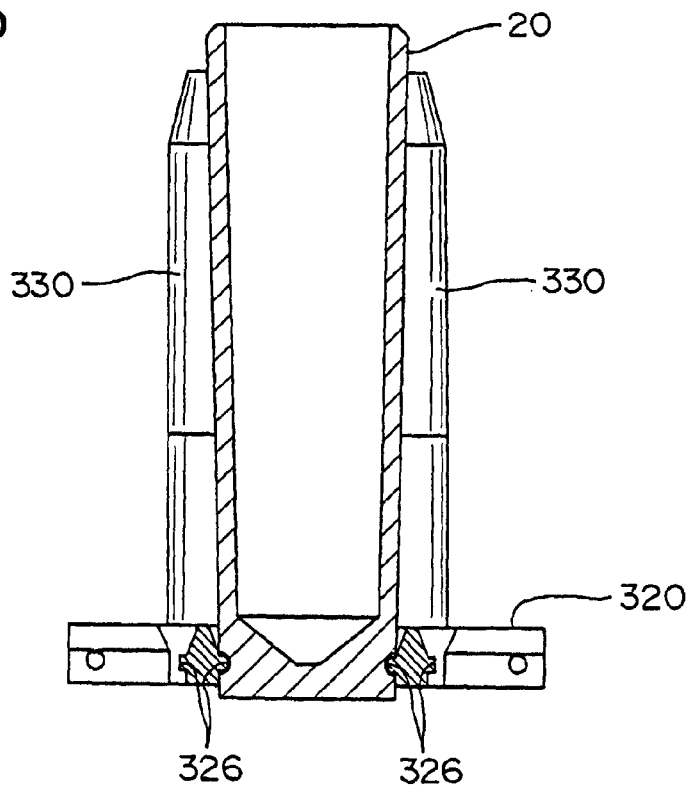

The storage frame composed of the grid bottom 320 is provided with container anchoring compressible protrusions 326 at inner side surfaces thereof as shown in FIGS. 9a and 9b and the container 20 is provided with container anchoring recesses 24 at the middle of the respective surfaces of the sidewalls 23 of the bottom thereof as shown in FIG. 8. The container anchoring projection 326 fits with the container anchoring recess 24 as a detent when the container 20 is stored in the storage rack 300, so that the container 20 will not fall out even if the storage rack 300 is turned around or inverted.

Figure 13:
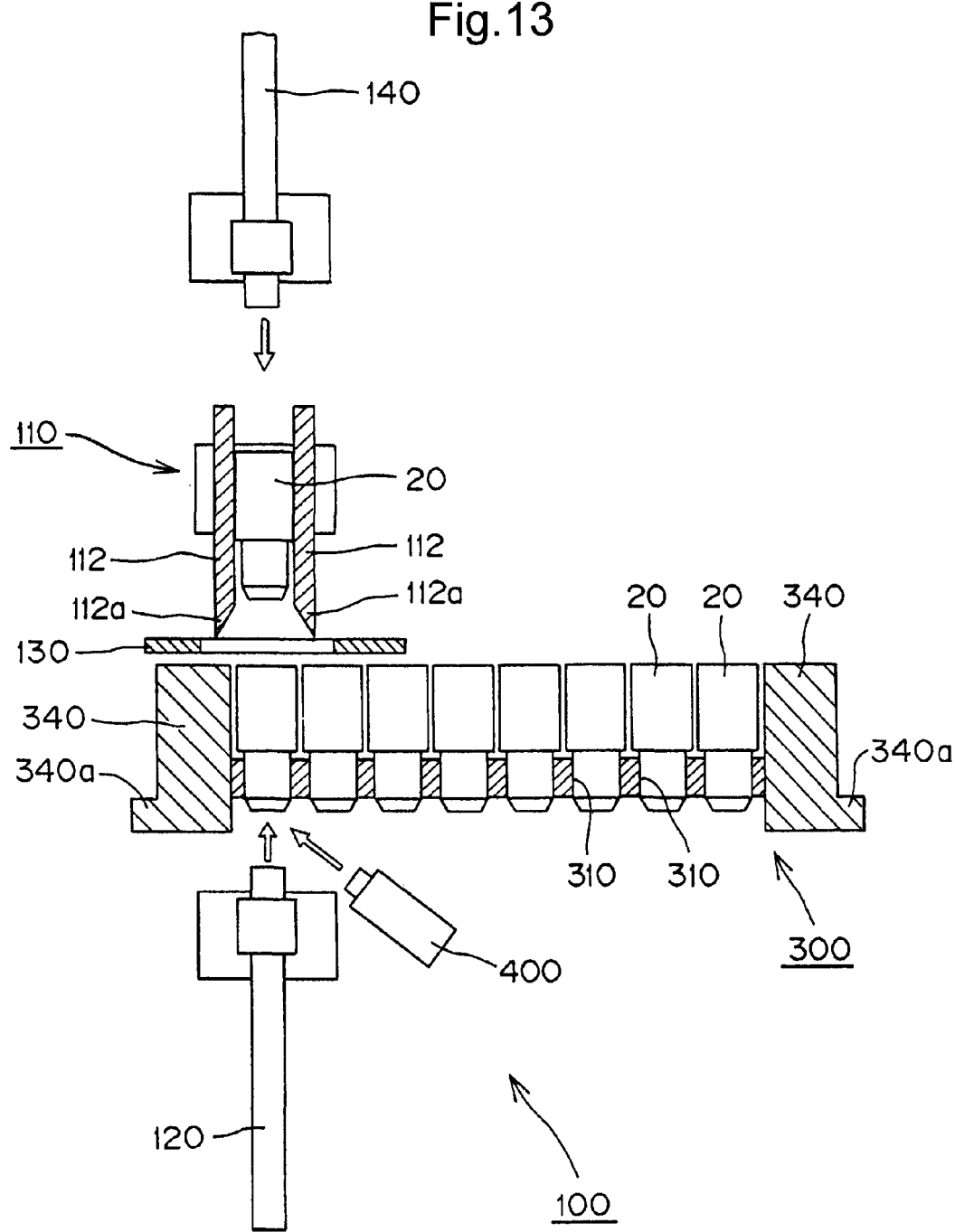
FIG. 13 is a conceptual drawing for explaining a mechanism of a picking operation of the pharmaceutical container transferring system of the invention.
Figure 14:
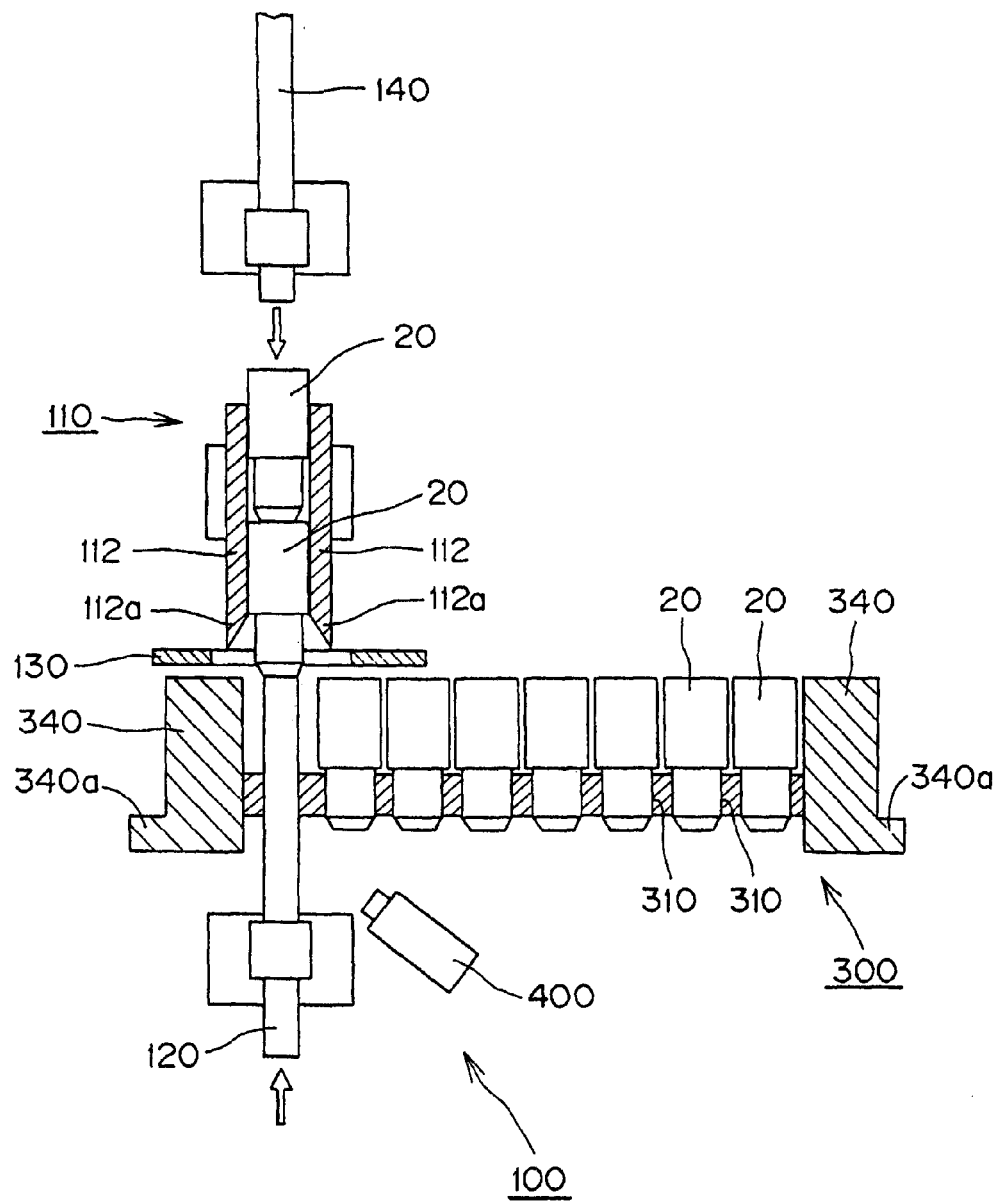
FIG. 14 is a conceptual drawing for explaining a mechanism of another picking operation of the pharmaceutical container transferring system of the invention.

Next, a mechanism of a picking operation of a transfer mechanism, i.e., one of technological feature of the pharmaceutical container transferring system 100 of the invention, will be explained. In FIGS. 13 and 14, a picking member 110 has spacing (a distance between confronting jaw members 112 in FIGS. 13 and 14) which is slightly smaller than a dimension of an upper part of the container 20. Each jaw member 112 is composed of a compressible material having enough elasticity even in very low temperature such as polypropylene so as to be able to pinch the incoming container 20 corresponding to a thrust-up operation of a thrust-up member 120. The jaw members 112 are formed such that the walls of the entry 112a are flared outwardly, so that the ingress of the container 20 may be readily carried out. Although the length of the jaw member 112 is enough if it has the length of the head of the container 20 to pick the container 20 one by one, the length of the jaw member 112 is prolonged to be longer than the whole length of the container 20 so that the jaw member 112 can pick up, stack and hold two or more selected containers as shown in FIG. 14. Thereby, the efficiency in transferring two or more containers to another storage rack may be enhanced.

In FIGS. 13 and 14, a co-lift preventing hold-down member 130 abuts against the upper surfaces of the heads of the surrounding containers to prevent the surrounding containers from being lifted up together with the container 20 thrust up by the thrust-up member 120. The hold-down member is formed into a donut shape having a hole for inserting one container 20 through the hold-down member 130 at the center thereof.

In FIGS. 13 and 14, a thrust-down member 140 thrusts the selected container 20 picked up by the picking member 110 down to a target storage position. The length of the thrust-down member 140 is different depending on a number of the containers 20 stored in the picking member 110 and when the picking member 110 holds many containers 20, the thrust-down member 140 is required to have a length that allows the last container 20 (the first pinched container) to be reliably thrust down.

The storage rack 300 is provided with the storage frame (insertion hole) 310 formed so as to fit with the shape of the lower part of the container 20. The storage rack 300 is also provided with a flange 340a formed around the peripheral edge of the bottom to reliably hold the bottom thereof on a storage rack mounting plate by one of the rack holding mechanisms as described later. Still more, in order to reliably identify each container 20, a two-dimensional code may be pasted or printed on the bottom of the container and a camera 400 may be installed at position near the thrust-up member 120 and facing to the bottom of the container 20 so that an image of the two-dimensional code on the bottom of the container 20 may be taken. It is also possible to arrange the thrust-up member 120 as an image detection section of the camera so as to take the image of the bottom of the container 20 during the thrust-up operation of the thrust-up member 120.

Figure 1:
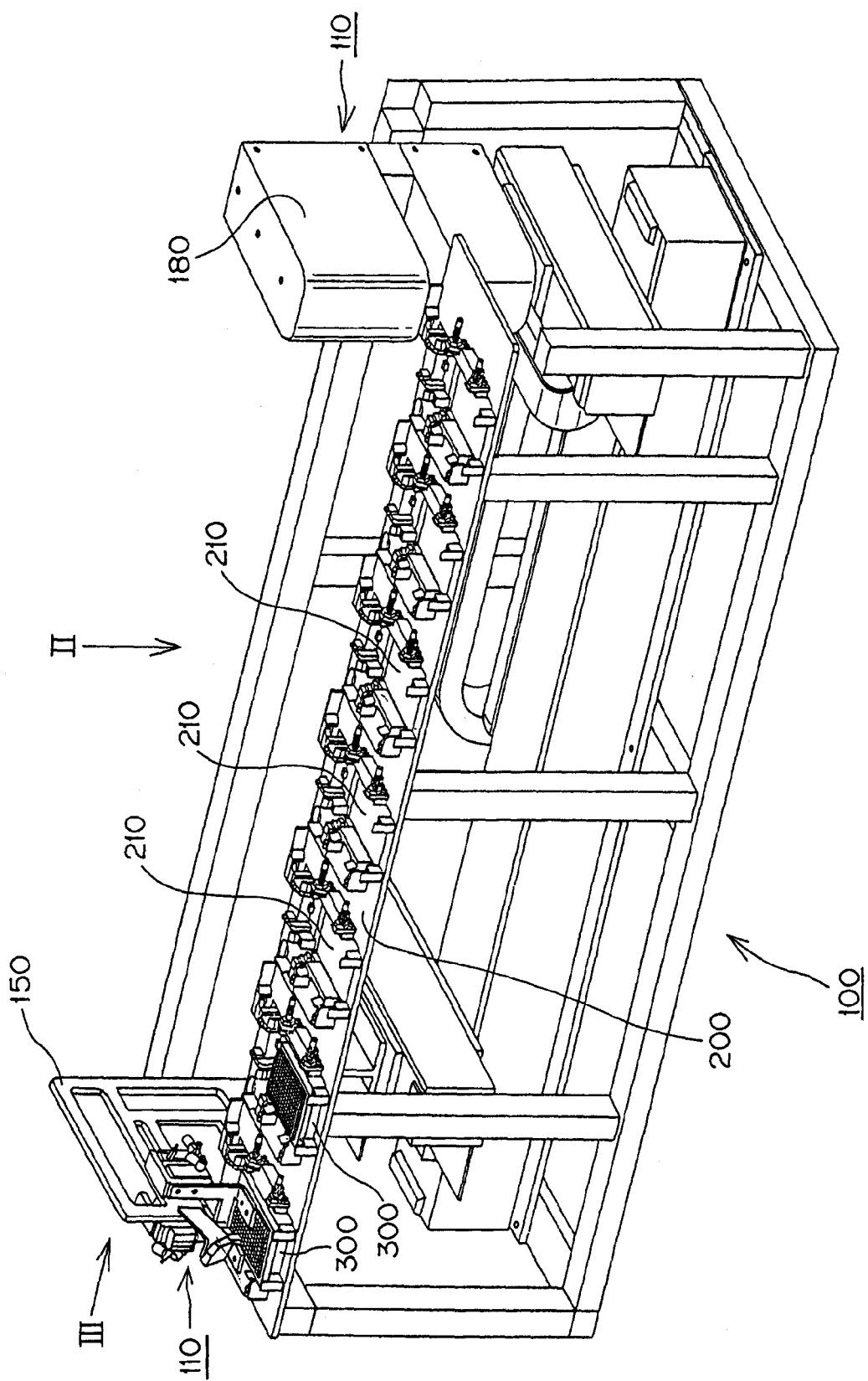
FIG. 1 is a perspective view showing an over-all appearance of a pharmaceutical container transferring system of the present invention.
Figure 2:
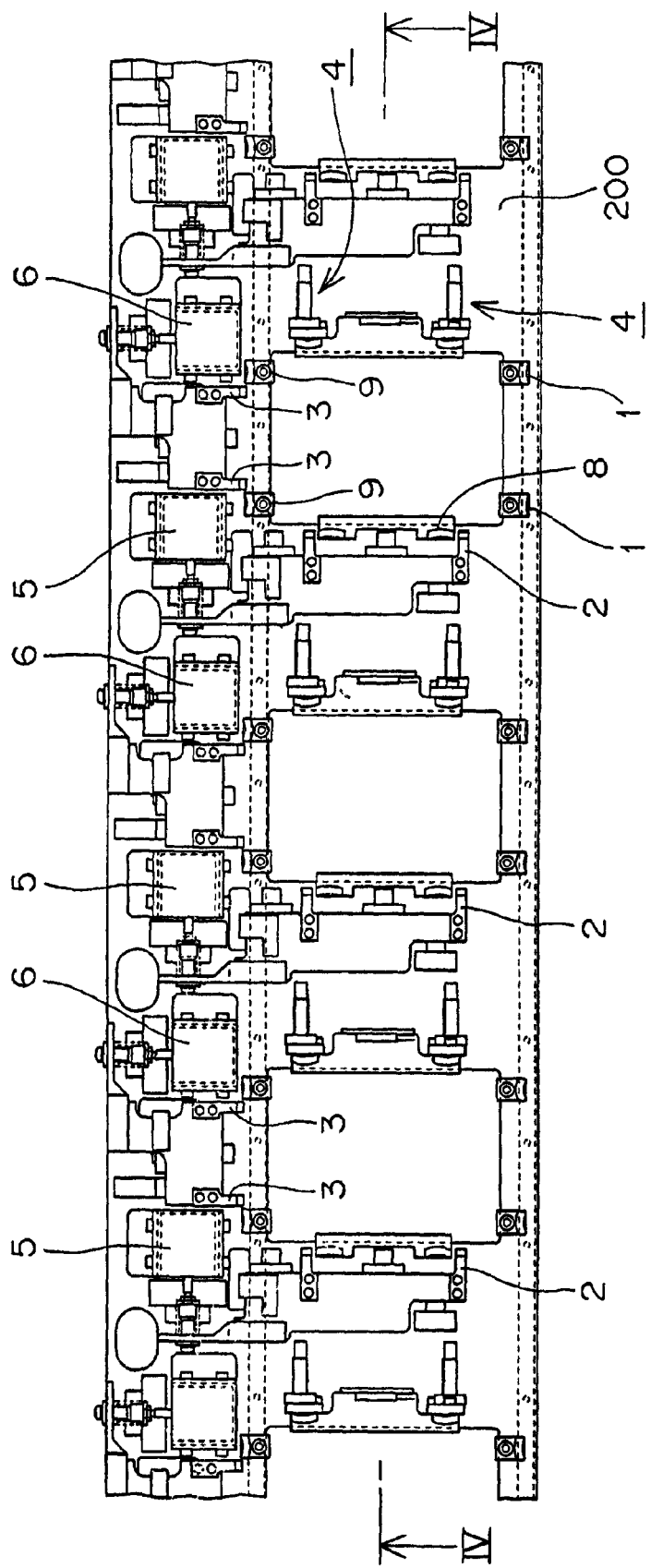
FIG. 2 is an upper plan view of the pharmaceutical container transferring system shown in FIG. 1 when seen from the direction of an arrow II.
Figure 3:
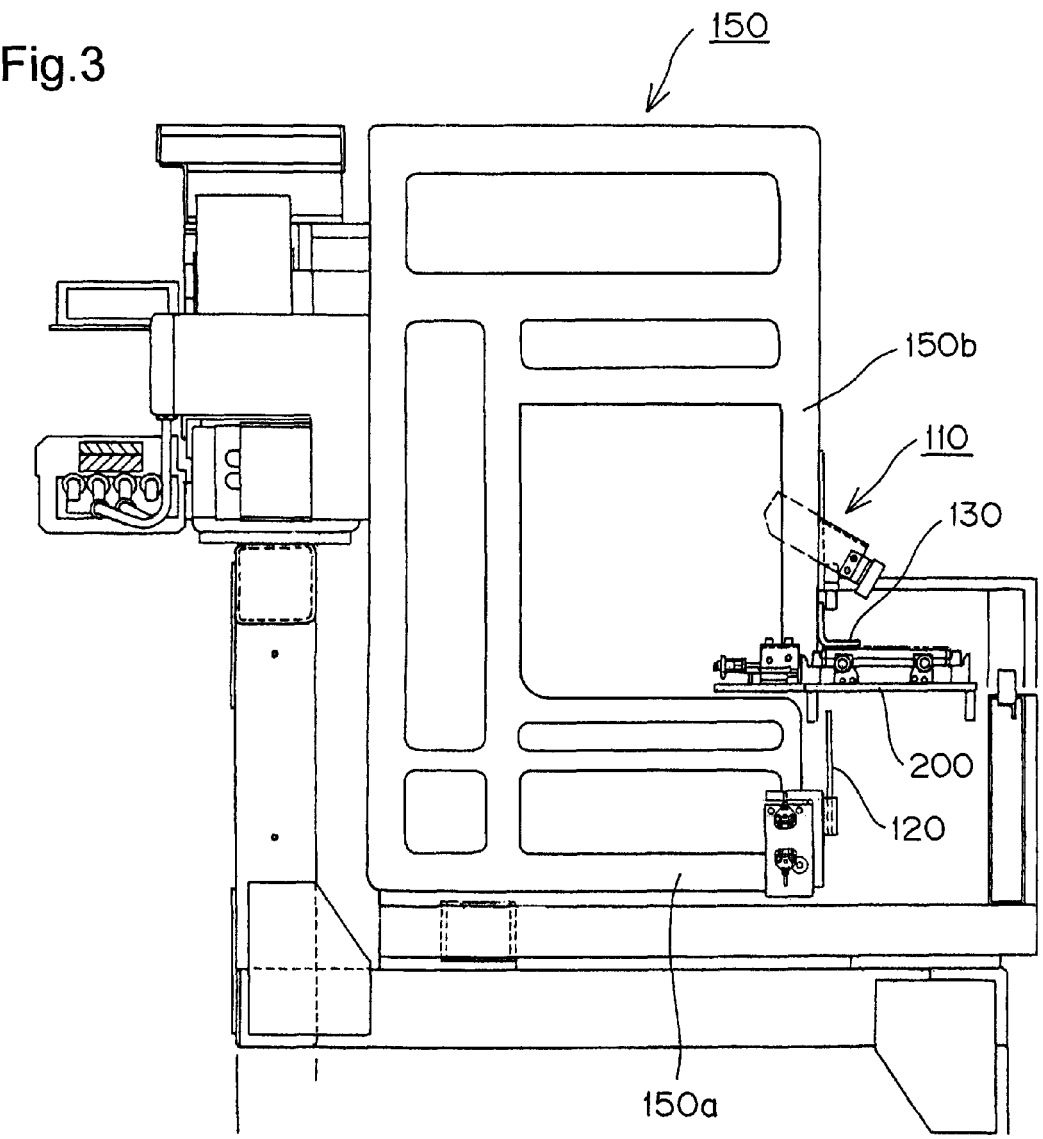
FIG. 3 is a side view of the pharmaceutical container transferring system shown in FIG. 1 when seen from the direction of an arrow III.
Figure 4:
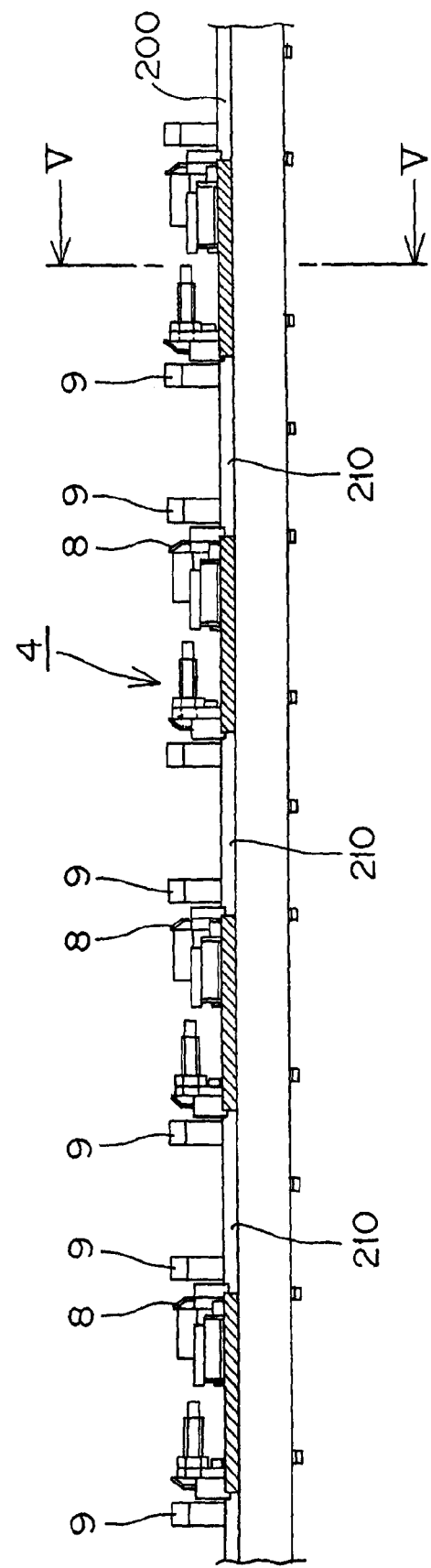
FIG. 4 is a section view taken along a line IV-IV of the pharmaceutical container transferring system shown in FIG. 2.
Figure 5:
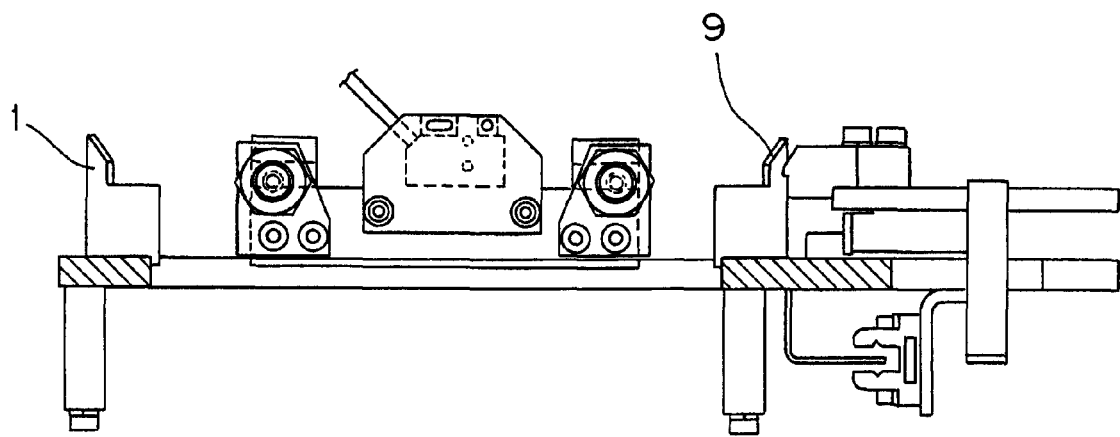
FIG. 5 is a section view taken along a line V-V of the pharmaceutical container transferring system shown in FIG. 4.

The thrust-up member 120 described above and the camera 400, as necessary, are attached to the side of a lower frame 150a of the picking carriage 150 shown in FIG. 3 and the co-lift preventing member 130, the picking member 110 and the thrust-down member 140 (not shown in FIG. 3) are attached to the side of an upper frame 150b of the picking carriage 150. Then, the picking carriage 150 is arranged to be movable on a horizontal plane while holding the storage rack 300 held by one of the rack holding mechanisms described later on the horizontally installed storage rack mounting plate so as to be able to take out and store a desired selected container 20 to a target storage position. It is noted that while the pharmaceutical container transferring system 100 that is one embodiment of the invention in FIG. 1 shows the storage rack mounting plate 200 having seven storage rack mounting areas 210, it is also possible to hold many more storage racks 300 by increasing the number of the storage rack mounting areas 210. As a result, the selected container 20 may be taken out of and stored in any target storage position among the large number of storage racks 300 regardless of source and destination of the transfer. Still more, because it is unnecessary to move the storage rack 300 in picking up the container 20, the system structure may be simplified and its space may be cut. Then, although the present embodiment shows the case of having the two transfer mechanisms, i.e., the picking members 110, the transfer mechanism may be one or may be three or more. It is noted that in FIG. 1, one of the two picking members 110 is shown in the state in which the case 180 is removed so that the structure of the picking member 110 may be readily understood.

Figure 6:
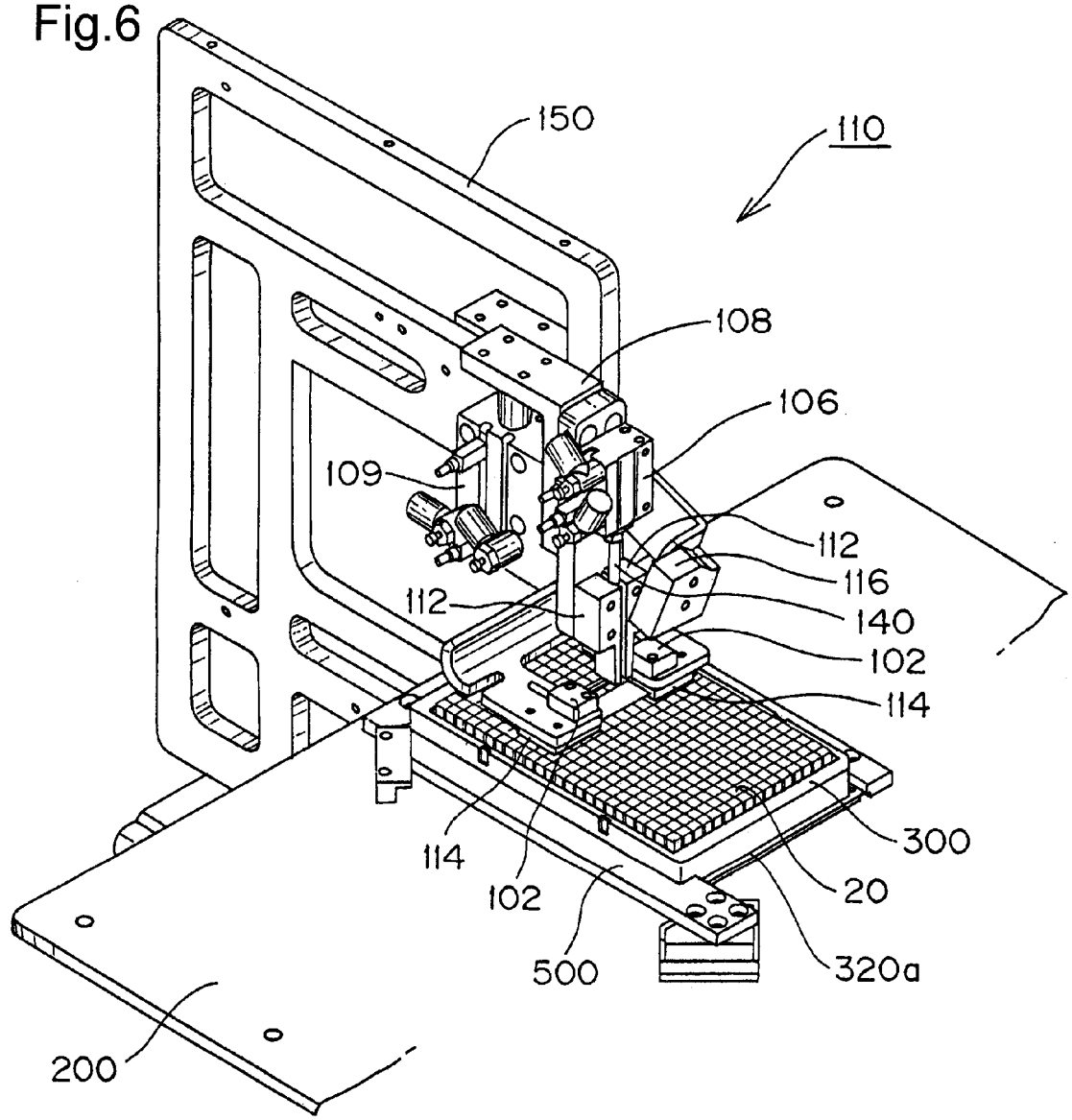
FIG. 6 is a perspective view of a transfer mechanism of the pharmaceutical container transferring system of the invention, showing a simplified rack holding system.
Figure 7:
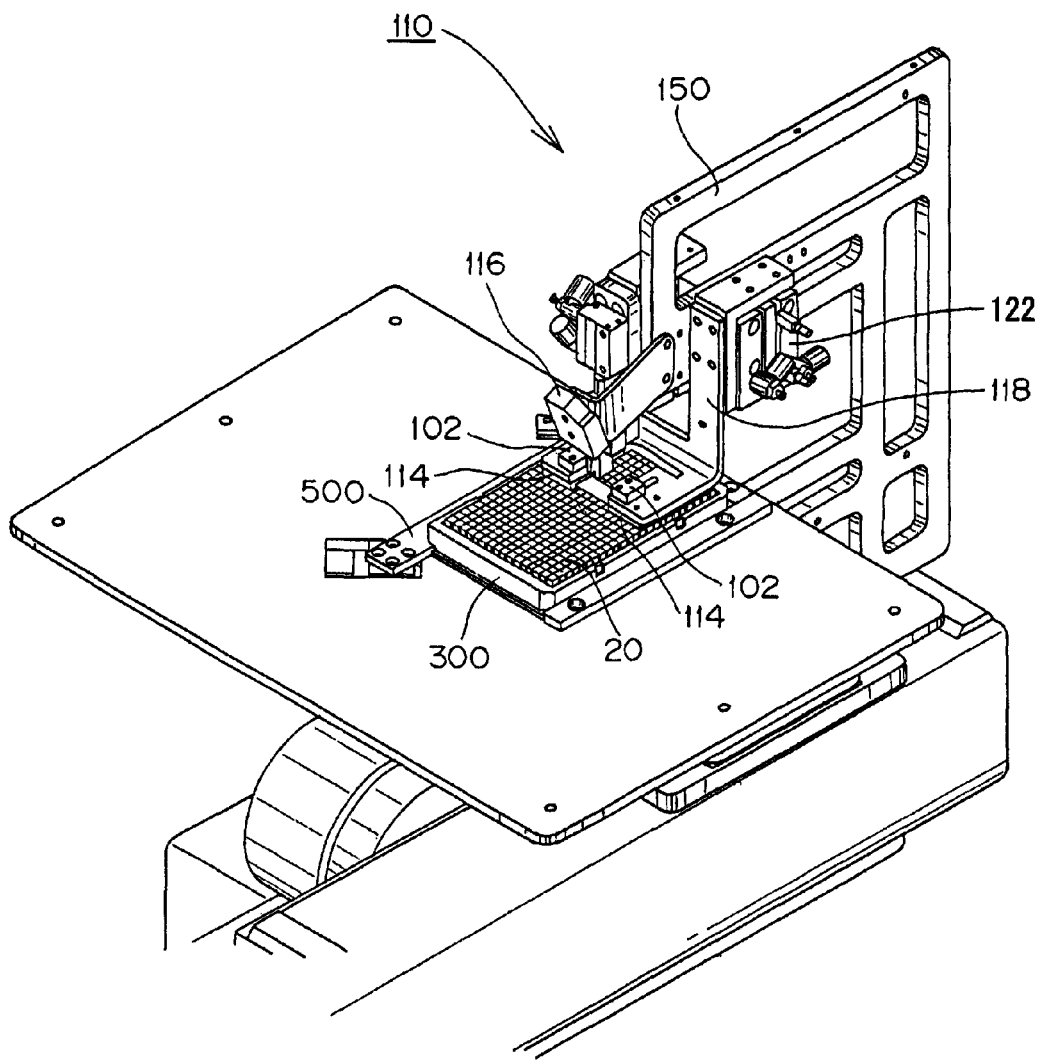
FIG. 7 is a perspective view of the transfer mechanism of the pharmaceutical container transferring system of the invention when seen from a different angle from that of FIG. 6.

FIGS. 6 and 7 are perspective views showing the structure of the transfer mechanism for realizing the picking operation described above. FIGS. 6 and 7 show a first rack holding mechanism having a simple mechanism for securing the flange 340a of the storage rack 300 by a storage rack fixing plate 500 and of screwing them to the storage rack mounting plate 200.

As it is apparent from FIG. 6, the pharmaceutical container transferring system 100 has the pair of jaw members 112 that confront to each other with a gap smaller than the width of the container 20, e.g., the 384-tube, that is to be transferred by the pharmaceutical container transferring system 100, and that are compressed to extend the width by their elastic deformation when the container 20 is pushed in from the underneath to pinch the container 20. The pharmaceutical container transferring system 100 also has the thrust-down mechanism for pushing the container 20 pinched by the jaw members 112 out of the jaw members 112 into a predetermined storage rack 300. This thrust-down mechanism is composed of the thrust-down member 140 that abuts against the head of the container 20 pinched by the jaw members 112 through the part between the pair of jaw members 112 and a thrust-down cylinder 106 for moving forward and back the thrust-down member 140.

A jaw member lifting mechanism is composed of a gripping cylinder moving section 108 and a gripping cylinder 109, and the thrust-down cylinder 106 and the jaw members 112 are secured to the gripping cylinder moving section 108. Then, due to the extension and retraction operation of the gripping cylinder 109, the gripping cylinder moving section 108 rises when the jaw members 112 grip and pull out the container 20 and when the picking carriage 150 transfers the container 20 to another place and drops when the jaw members 112 inserts the container 20 gripped by the jaw members 112 in the storage rack 300 and when the container 20 is pulled out of the storage rack 300.

FIG. 7 is a perspective view when the pharmaceutical container transferring system 100 of the invention is seen from a direction different from FIG. 6. A grasp confirming sensor 102 detects whether or not the target container 20 is firmly gripped by the jaw members 112. Specifically, the grasp confirming sensor 102 uses a line sensor that enables the operator to confirm whether or not an object exists by a light beam whether or not it is transmitted. When the jaw members 112 grip the container 20, the light beam is blocked, so that it is confirmed that the container 20 exists.

A pair of co-lift preventing sensors 114 detect as abnormal when the containers around the target container 20 are lifted together by adhering to the target container 20 or the jaw member 112 due to freezing or the like. The co-lift preventing sensor 114 uses an area sensor having a detection width wider than that of the container to confirm whether or not there are other containers around the target container 20 and detects as abnormal because light is blocked when the containers around the target container 20 rise together. The co-lift preventing sensor 114 is installed at height within the width of the container 20 from the top of the container 20 stored in the storage rack so that it can detect when the co-lifted tube falls down. Meanwhile, the jaw member lifting mechanism is set so that a lifting distance of the jaw members 112 is less than a length obtained by adding the length of the container 20 to the width of the container 20 (setting height of the co-lift preventing sensor 114) so that the co-lifted container will not be located above the detection area of the co-lift preventing sensor 114 and becomes undetectable.

A double insertion preventing sensor 116 detects whether or not there exists the container 20 within one section of the storage rack 300 to which the jaw members 112 face. The double insertion preventing sensor 116 utilizes a reflection-type sensor whose sensitivity changes depending on a distance of a light beam irradiated and returned by being reflected by an object. The double insertion preventing sensor 116 detects reflection from the top of the container 20 and prevents double insertion only when the container 20 exists in one section of the storage rack 300 to which the jaw members 112 face.

A sensor lift mechanism is composed of a sensor lifting cylinder moving section 118 and a sensor lifting cylinder 122, and the co-lift preventing sensor 114 and a grasp confirming sensor 102 installed near the storage rack 300 are fixed to the sensor lifting cylinder moving section 118. Then, the sensor lifting cylinder moving section 118 lifts the co-lift preventing sensor 114 and the grasp confirming sensor 102 by the expansion and contraction operation of the sensor lifting cylinder 122 so that they do not hit against any fallen object on the storage rack 300 or the container 20 protruding due to improper insertion during traveling of the picking carriage 150.

As described above, according to the transfer mechanism provided in the pharmaceutical container transferring system 100 of the invention, only the picking carriage 150 moves in picking up the container 20 and the container thrust-up and thrust-down operations may be carried out only by the cylinders that conduct the simple rectilinear movement, so that the system structure and the control are simplified and may be realized at low cost.

A second rack holding mechanism that is a further technological feature of the pharmaceutical container transferring system 100 of the invention will be explained next.

Figure 10:
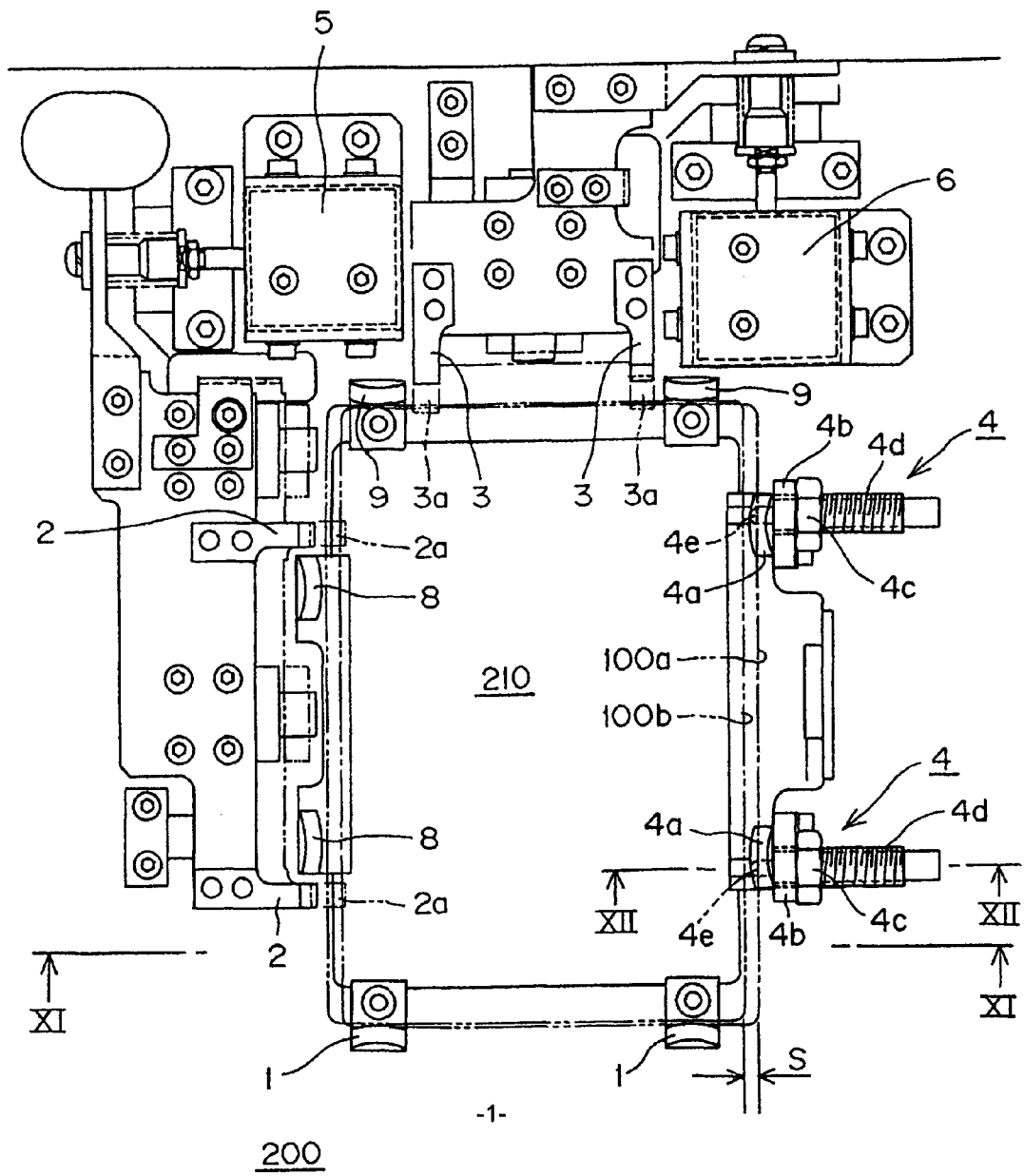
FIG. 10 is a plan view of an adjustable rack holding mechanism of the invention.

FIG. 10 is a front view of the second rack holding mechanism. Substantially rectangular frames 100a and 100b drawn by two-dot chain lines in the middle of the figure indicate the outermost edge of the storage rack, wherein the line 100a indicates position when the storage rack is grasped and the line 100b indicates position when the storage rack is released.

The rack holding mechanism has two stationary guides 1 for supporting the storage rack by pressing one side surface of a short side of the storage rack in holding the storage rack. The rack holding mechanism also has movable floating preventing claws 2 that movably face to the long side of the storage rack and that engage with the flange of the storage rack and movable floating preventing claws 3 that face to the opposite short side of the storage rack at two neighboring side surfaces different from one side surface described above. The movable floating preventing claw 2 are movably driven by an actuator 5 and the movable claw members 3 are movably driven by an actuator 6. It is noted that the reference numerals 2a and 3a indicate the position of the movable floating preventing claws 2 and 3 when they are moved forward. Still more, the stationary guides 1 restrict the storage rack from moving when the movable floating preventing claws 3 move forward, i.e., when the storage rack is grasped, and have no function of engaging with the flange of the storage rack.

Then, the rack holding mechanism has stationary floating preventing claws 4 that face to the opposite side surface (long side) and contain extrusion pins biased by springs that contract by abutting against the flange of the storage rack when the movable floating preventing claws 2 move forward and that push back the flange of the storage rack by expanding when the movable floating preventing claws 2 retract. It is noted that storage rack guiding members 8 and 9 cooperate with the guides 1 to guide the storage rack into position on the mounting plate 200.

Figure 11A:
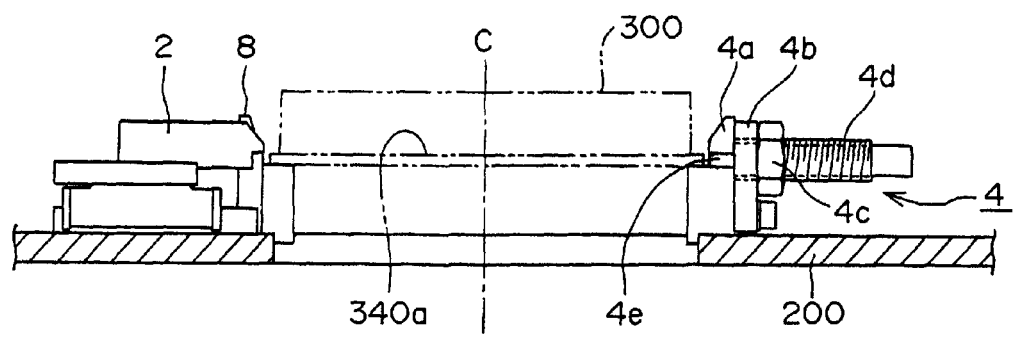
FIGS. 11a and 11b are section views of the adjustable rack holding mechanism taken along a line XI-XI in FIG. 10, FIG. 11a showing the positions of the movable claws prior to their movement toward one another and FIG. 11b showing their positions after their movement toward one another.
Figure 11B:
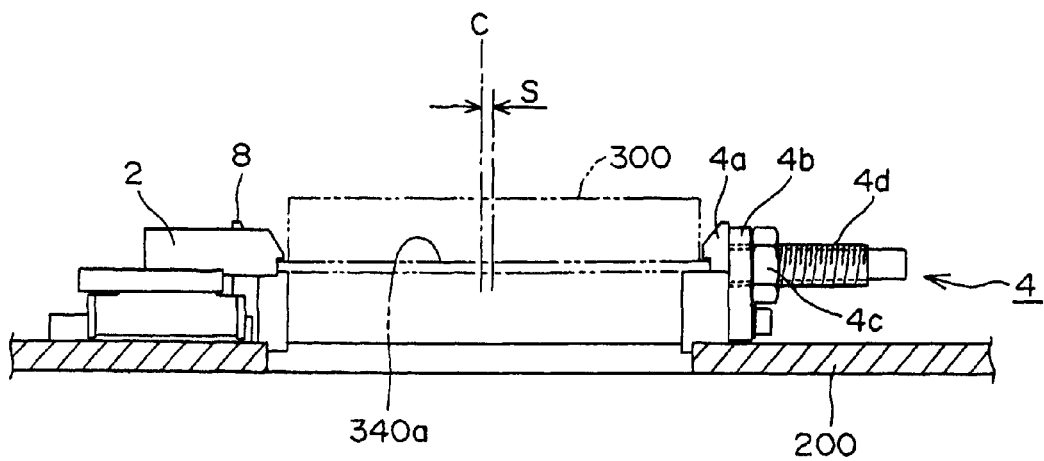

FIGS. 11a and 11b are section views taken along a line XI-XI of the rack holding mechanism shown in FIG. 10, wherein FIG. 11a shows a state when the rack is released and FIG. 11b shows a state when the rack is held. In FIGS. 11a and 11b, a dashed line C is a center line of the storage rack mounting area of the mounting plate 200. As shown in FIG. 11a, when the storage rack is released, the movable floating preventing claw 2 retracts and the engagement with the flange 340a of the storage rack 300 is released. The extrusion pin 4e of the stationary floating preventing claw 4 also is protruded by the spring 4h (shown in FIG. 12), pushes back the flange 340a of the storage rack 300 and disengages the engagement of an anchoring member 4a with the flange 340a of the storage rack 300. Accordingly, the storage rack 300 may be moved in the vertical direction without being interfered by the anchoring members and others in taking the storage rack 300 out of the rack holding mechanism.

When the rack is grasped on the other hand, the movable floating preventing claw 2 moves forward and engages with the flange 340a of the storage rack 300 and moves the storage rack 300 in the direction of the stationary floating preventing claw 4 by a distance S as shown in FIG. 11b. As a result, the flange 340a of the storage rack 300 abuts against the extrusion pin 4e, the extrusion pin 4e retracts and the anchoring member 4a of the stationary floating preventing claw 4 engages with the flange 340a of the storage rack 300.

Accordingly, when the rack is grasped, the movable floating preventing claw 2 presses the storage rack 300 against the anchoring member 4a of the stationary floating preventing claw 4 and the movable floating preventing claw 3 presses the rack against the stationary guide 1, so that the storage rack 300 is grasped and is positioned. Still more, because what are necessary to be driven to grasp the storage rack 300 are only the movable floating preventing claws 2 and 3 facing to the neighboring two side surfaces of the storage rack 300, only the two actuators 5 and 6 are necessary as driving sources. Therefore, the space and cost of the rack holding mechanism may be cut.

Figure 12:
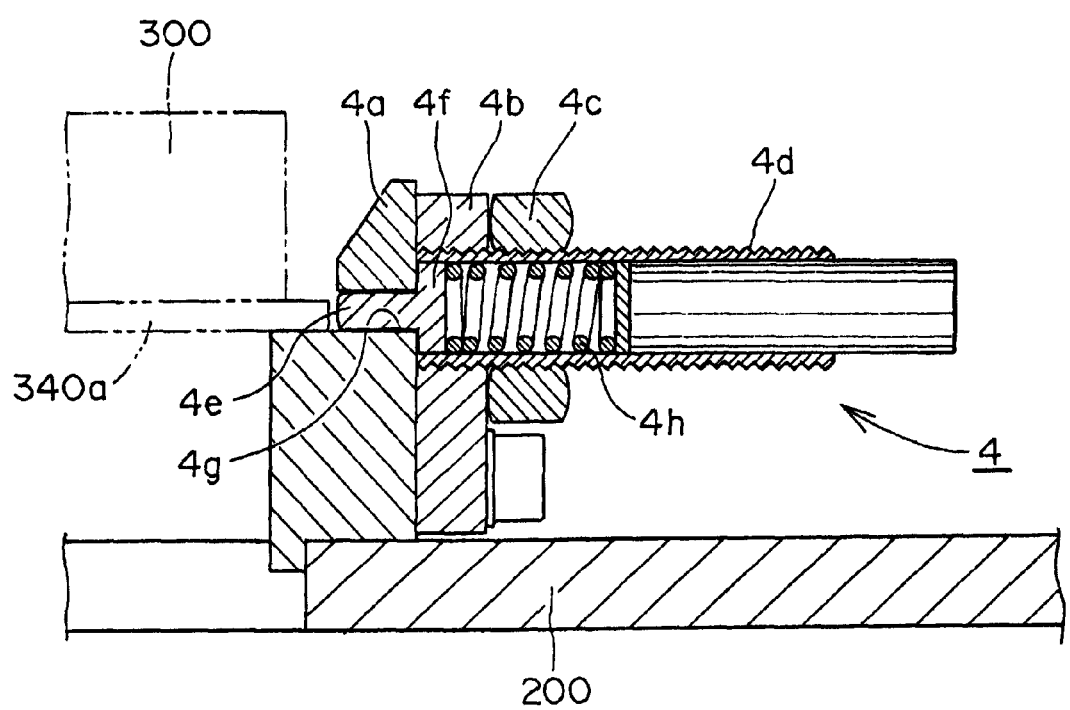
FIG. 12 is a section view of a part of the rack holding mechanism taken along a line XII-XII in FIG. 10.

Next, the internal structure of the stationary floating preventing claw 4 will be explained with reference to FIG. 12. The stationary floating preventing claw 4 has the anchoring member 4a having a groove that engages with the flange 340a of the storage rack 300, a claw securing member 4b for securing the anchoring member 4a to the storage rack mounting plate 200 of the rack holding mechanism, a hollow screw member 4d threaded into the claw securing member 4b, a nut 4c composing a double nut mechanism for fixing the hollow screw member 4d to the claw securing member 4b, the extrusion pin 4e movably inserted from the side of the member 4d through the insertion hole 4g in the middle of the groove that is provided in the anchoring member 4a and that engages with the flange 340a of the storage rack 300 and provided perpendicularly to a top board 4f and a spring 4h inserted within the hollow screw member 4d to abut against the head 4f of the extrusion pin 4e and to bias the extrusion pin 4e.

As described above, the rack holding mechanism provided in the pharmaceutical container transferring system 100 of the invention enables to fix and position the storage rack accurately by the floating preventing claws from the three directions, i.e., by the movable floating preventing claws from the two directions and the stationary floating preventing claw from one direction. Still more, when the storage rack is released, the storage rack is released from all of the claw members and may be lifted, so that the storage rack may be automatically suitably transferred. Thus, in conjunction with the effects brought about by the transfer mechanism described above, the pharmaceutical container transferring system of the invention has such remarkable effects that the operation may be speeded-up, the reliability may be improved and the space of the system may be cut.

INDUSTRIAL APPLICABILITY

The pharmaceutical container transferring system of the invention realizes the mechanization of the operations for taking out and storing the containers stored in the 384-tube rack which have been considered to be difficult heretofore with the simple system structure, so that its industrial applicability is extremely high.

The invention claimed is:

1. The A pharmaceutical container transferring system including containers for samples for pharmaceutical development and a storage rack vertically storing a plurality of said containers in a matrix, said storage rack having insertion holes that fit the shape of the lower part of said container to support said container, said system further comprising:
a picking carriage adapted for taking a selected container out of said storage rack or for storing a container into a target storage position within said storage rack,
a rack holding mechanism having a mounting plate dimensioned for holding said storage rack in a horizontal position in a rack-holding area;
a lower thrust-up member provided underneath of said storage rack mounting plate positioned to thrust up the container through the insertion hole of said storage rack while abutting with the bottom of the selected container;
an upper picking member provided above said storage rack mounting plate and having compressible jaw members spaced apart with spacing smaller than the dimension of the upper part of said thrust-up container to pinch the incoming container corresponding to the thrust-up operation of the thrust-up member by compressing said jaw members to extend their spacing by extending its width; and
an upper thrust-down member disposed in vertical registry with said thrust-up member for thrusting down the container pinched by said picking member;
said picking carriage mounting said lower thrust-up member, said upper picking member and said upper thrust-down member, said carriage adapted to move while sandwiching said storage rack mounting plate between said lower and upper members.

2. The pharmaceutical container transferring system according to claim 1, wherein the vertical length in the longitudinal direction of said jaw member is longer than the whole length of the container.

3. The pharmaceutical container transferring system according to claim 1, said carriage further comprising a hold-down member adapted to be disposed above said storage rack mounting plate to abut with the upper surface of the head of the containers surrounding the selected container so that the surrounding containers are not lifted up together with the selected container thrust-up by said thrust-up member.

4. The pharmaceutical container transferring system according to claim 1, wherein said storage rack mounting plate has a plurality of storage rack mounting areas for holding said racks in horizontal positions at a plurality of rack-holding mounting areas, said rack holding mechanisms being disposed at each of the respective storage rack mounting areas.

5. The pharmaceutical container transferring system according to claim 4, wherein the vertical length in the longitudinal direction of said jaw member is longer than the whole length of the container.

6. The pharmaceutical container transferring system according to claim 4, further comprising a hold-down member adapted to be disposed above said storage rack mounting plate to abut with the upper surface of the head of the containers surrounding the selected container so that the surrounding containers are not lifted up together with the selected container thrust-up by said thrust-up member.

7. The pharmaceutical container transferring system according to claim 4 for use with a storage rack comprising a flange around peripheral edge of the bottom thereof; wherein:
said rack holding mechanism comprises stationary guides for pressing and supporting one side surface of said storage rack;
movable floating preventing claws provided so as to movably face the storage rack at two neighboring side surfaces different from said one side surface of said storage rack and engaging with said flange of said storage rack when said claws move forward; and
stationary floating preventing claws facing a side of the storage rack opposite to at least one of said two neighboring side surfaces, said stationary claws containing extrusion pins that abut with the flange of said storage rack and contract when said movable floating preventing claws move forward to displace said storage rack against said stationary floating preventing claws, and extend when said movable floating preventing claws retract, said extended extrusion pins operating to push back the flange of said storage rack.

8. The pharmaceutical container transferring system according to claim 7 in which said container has a container anchoring recess on the sidewall of the bottom thereof; and
said storage rack has a container-anchoring projection on the inner side surface of the through hole; and said container anchoring recess mating with said container anchoring projection when said container is stored in said storage rack.

9. The pharmaceutical container transferring system according to claim 1, in which said container has a container anchoring recess on the sidewall of the bottom thereof; and said storage rack has a container-anchoring projection on the inner side surface of the through hole;

said container anchoring recess mating with said container anchoring projection when said container is stored in said storage rack.

10. A pharmaceutical container transferring system for use with containers for samples for pharmaceutical development and a storage rack for vertically storing a plurality of said containers in a matrix, said storage rack having insertion holes that fit the shape of the lower part of said container to support said container, said system comprising:

a picking carriage dimensioned for taking a selected container out of said storage rack or for storing a container into a target storage position within said storage rack, a rack holding mechanism having a mounting plate dimensioned for holding said storage rack in a horizontal position in a rack-holding area;

a lower thrust-up member provided underneath of said storage rack mounting plate dimensioned to thrust up the container through the insertion hole of said storage rack while abutting with the bottom of the selected container;

an upper picking member provided above said storage rack mounting plate and having compressible jaw members spaced apart with spacing smaller than the dimension of the upper part of said thrust-up container to pinch the incoming container corresponding to the thrust-up operation of the thrust-up member by compressing said jaw members to extend their spacing by extending its width; and an upper thrust-down member disposed in vertical registry with said thrust-up member for thrusting down the container pinched by said picking member;

said picking carriage mounting said lower thrust-up member, said upper picking member and said upper thrust-down member, said carriage adapted to move while sandwiching said storage rack mounting plate between said lower and upper members.

* * * * *